(12) United States Patent
Ryan et al.

(10) Patent No.: US 12,005,242 B2
(45) Date of Patent: Jun. 11, 2024

(54) HINGED NEEDLE SHIELD AND NEEDLE ASSEMBLIES

(71) Applicant: Becton, Dickinson and Company, Franklin Lakes, NJ (US)

(72) Inventors: Kevin M. Ryan, Whitehouse Station, NJ (US); Angela Huenerfauth, Morristown, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 44 days.

(21) Appl. No.: 17/179,088

(22) Filed: Feb. 18, 2021

(65) Prior Publication Data
US 2021/0260304 A1 Aug. 26, 2021

Related U.S. Application Data

(60) Provisional application No. 62/979,797, filed on Feb. 21, 2020.

(51) Int. Cl.
*A61M 5/32* (2006.01)
*A61M 5/34* (2006.01)

(52) U.S. Cl.
CPC ........ *A61M 5/3202* (2013.01); *A61M 5/3293* (2013.01); *A61M 5/346* (2013.01); *A61M 5/348* (2013.01)

(58) Field of Classification Search
CPC ........ A61M 5/3202; A61M 2005/3217; A61M 5/3216; A61M 5/3293; A61M 5/346; A61M 5/348
See application file for complete search history.

(56) References Cited

U.S. PATENT DOCUMENTS

| 5,154,285 A | * | 10/1992 | Hollister | A61B 5/154 |
| | | | | 206/365 |
| 5,665,075 A | * | 9/1997 | Gyure | A61M 5/3202 |
| | | | | 604/263 |
| 11,033,213 B2 | * | 6/2021 | Wang | A61B 5/153 |
| 2002/0193744 A1 | | 12/2002 | Alesi et al. | |

FOREIGN PATENT DOCUMENTS

| EP | 0626924 B1 | 5/1998 |
| KR | 101940275 B1 | 9/2018 |

OTHER PUBLICATIONS

PCT International Search Report and Written Opinion in PCT/US2021/018722 dated Jun. 11, 2021, 23 pages.

* cited by examiner

*Primary Examiner* — Theodore J Stigell
*Assistant Examiner* — Rachel T. Smith
(74) *Attorney, Agent, or Firm* — Servilla Whitney LLC (57) ABSTRACT

A needle shield assembly for use with a needle assembly is disclosed. The needle shield assembly includes an elongate needle shield comprising a shield portion, a hub connection portion and a bridge portion including a living hinge having a thickness. The bridge portion joins the hub connection portion and the shield portion. The hub connection portion includes a partially circular receiving ring having a diameter sized to frictionally receive a flange of a hub of the needle assembly. The shield portion includes two longitudinal walls defining a cavity and a needle assembling receiving cavity between the two longitudinal walls defining a recess. The shield portion is configured to pivot from an open position in which a needle cannula is exposed, to a closed needle protecting position in which a distal end of the needle cannula is within the longitudinal opening of the shield.

19 Claims, 13 Drawing Sheets

HINGED NEEDLE SHIELD AND NEEDLE ASSEMBLIES

CROSS-REFERENCE TO RELATED APPLICATIONS

This application claims priority to U.S. Provisional Application No. 62/979,797, filed Feb. 21, 2020, the entire disclosure of which is hereby incorporated by reference herein.

TECHNICAL FIELD

The present disclosure generally relates to needle assemblies having safety features and more specifically to a needle assembly having a hinged needle shield assembly for use with a syringe.

BACKGROUND

Accidental needle sticks with new unused needle can cause injury and render the needle unfit for further use. Accidental needle sticks with a used needle can transmit disease. As a result, prior art needle assemblies have a needle shield. Some prior art needle shields define a rigid sleeve that can be manually telescoped over a needle cannula. This procedure requires a healthcare worker to hold the syringe barrel in one hand and the shield in the other. Some medical procedures require the application of pressure to the penetration site after the needle has been removed. Thus, healthcare workers are often unable to use both hands for shielding the needle cannula. In these situations, workers merely deposit the used medical implement on a nearby surface with the intention of shielding at a more convenient time. However, until the needle is shielded or properly disposed of, it presents a potential danger to other people.

A needle shield which is hinged near the base of the needle has the advantage of allowing one-handed needle reshielding, providing the opportunity for reshielding by a medical practitioner, under most circumstances, immediately after use.

Various means have been provided for locking a hinged needle shield in the closed, needle protecting position. Deflectable members have been provided in the needle shield for engaging the needle upon shielding and preventing subsequent unshielding of the needle. Such members trap the needle within the needle shield. Locking has also been accomplished by locking engagement of the needle shield with structure near the base of the needle.

Hinged needle shields and syringes are commonly packaged and manufactured together as a needle shield assembly or a combined package. However, because needle shield assemblies rely on direct and specific fitment of the hinged needle shield to the needle assembly, the rate of production (throughput) is significantly lower than conventional (non-safety shield) needles. The reason for this is that the manufacturing assembly has to rotationally align the needle cannula such that the needle bevel is in the correct (user friendly) orientation in relation to the safety shield orientation. Further, separate manufacturing lines from the conventional needles lead to higher manufacturing.

Thus, there is still a need for an improved hinged needle shield that is cost effective and easy to manufacture.

SUMMARY

One aspect of the present disclosure relates to a needle shield assembly for use with a needle assembly having a shield portion, a hub connection portion, and a bridge portion. In one or more embodiments, the shield portion includes two longitudinal walls extending from a base of the shield portion, the two longitudinal walls being separated by a needle assembly receiving cavity. The needle assembly receiving cavity is defined by the base, the two longitudinal walls and an open end opposite the base, the two longitudinal walls and the needle assembly receiving cavity are configured to receive a needle assembly. In one or more embodiments, a proximal portion of the needle assembly receiving cavity is wider than a distal portion of the needle assembly receiving cavity, the proximal portion of the needle assembly receiving cavity receives a hub of the needle assembly and the distal portion of the needle assembly receiving cavity receives a cannula of the needle assembly. The hub connection portion includes a partially circular receiving ring having a substantially crescent shape, an arc of the crescent shape has a length that is greater than a length of a semicircle having a same radius as the arc, wherein the partially circular receiving ring deflects or elastically deforms outwardly upon advancement of a receiving flange of the needle assembly, the partially circular receiving ring locks the receiving flange of the needle assembly within. In one or more embodiments, the bridge portion connects the shield portion and the hub connection portion, the bridge portion comprising a hub connection portion and a bridge portion and a living hinge. In one or more embodiments, the bridge portion joins the hub connection portion and the shield portion.

In one or more embodiments, the hub connection portion includes the partially circular receiving ring having an inner diameter sized to frictionally receive and engage the receiving flange of the hub of the needle assembly when the needle shield assembly is advanced against the receiving flange in an axial direction towards the needle assembly. In one or more embodiments, the receiving flange of the hub of the needle assembly and the hub connection portion of the needle shield assembly engage in an interference fit.

In one or more embodiments, at least one locking hook is disposed within the proximal portion of the needle assembly receiving cavity. In some embodiments, there are two locking hooks, a first locking hook and a second locking hook.

In one or more embodiments, a first of the at least one locking hook is in a plane, and a second of the at least one locking hook is in the plane, the at least one locking hook comprising a protrusion extending from the base.

In one or more embodiments, at least one locking hook is configured to deflect or elastically deform upon engagement with the needle cannula, the at least one locking hook having a pointed end which first engages the needle cannula.

In one or more embodiments, the bridge portion includes a first portion and a second portion, each of the first portion and the second portion comprising a width and the living hinge comprising a thickness, the thickness being sufficient to allow the living hinge to flex and bend.

In one or more embodiments, the shield portion pivots against the living hinge. In one or more embodiments, the shield portion pivots from an open position to a closed position. In one or more embodiments, the shield portion is in the closed position when the needle cannula of the needle assembly is fully disposed within the needle assembly receiving cavity.

In one or more embodiments, the partially circular receiving ring includes a recess.

In one or more embodiments, the recess forms a U-shaped cross section within the partially circular receiving ring of the hub connection portion. In one or more embodiments, the recess defines a first diameter and a second diameter that is less than the first diameter.

In one or more embodiments, the receiving flange of the needle assembly is received within the partially circular receiving ring of the needle shield assembly, the partially circular receiving ring deflects or elastically deforms from an initial state upon advancement of the receiving flange and snap-fits the receiving flange upon full advancement, wherein the partially circular receiving ring deflects or elastically deforms back into the initial state.

In one or more embodiments, a snap-fit fitment between the receiving flange and the partially circular receiving ring allows for retention of the receiving flange within the partially circular receiving ring. In one or more embodiments, the snap-fit fitment allows for twisting and angular movement of the partially circular receiving ring around the receiving flange.

In one or more embodiments, the partially circular receiving ring envelopes more than half of a profile of the receiving flange of the hub of the needle assembly, the receiving flange being in the form of a circular protrusion extending from the outer surface of the needle assembly. In one or more embodiments, the circular protrusion of the hub of the needle assembly sits within the recess of the partially circular receiving ring.

DETAILED DESCRIPTION

While this disclosure is satisfied by embodiments in many different forms, there are shown in the drawings and will herein be described in specific embodiments of the disclosure with the understanding that the present disclosure is to be considered exemplary of the principles and are not intended to limit the disclosure to the embodiments illustrated. The scope of the disclosure will be measured by the appended claims and their equivalents.

As used herein, the use of "a," "an," and "the" includes the singular and plural.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on a vascular access device (VAD). A Luer connector also has a distal end channel that releasably attaches the Luer connector to the hub of a VAD, and a proximal end channel that releasably attaches the Luer connector to a barrel of a syringe.

As used herein, ISO 80369-7:2016 defines a specification for standard Luer connectors including a 6% taper between the distal end and the proximal end. A male standard luer connector increases from the open distal end to the proximal end. A female standard luer connector decreases from the open proximal end to the distal end. According to ISO 80369-7:2016, a male standard luer connector has an outer cross-sectional diameter measured 0.75 mm from the distal end of the tip of between 3.970 mm and 4.072 mm. The length of the male standard luer taper is between 7.500 mm to 10.500 mm. The outer cross-sectional diameter measured 7.500 mm from the distal end of the tip is between 4.376 mm and 4.476 mm. As used herein, the phrases "male standard luer connector" and "female standard luer connector" shall refer to connectors having the dimensions described in ISO 80369-7, which is hereby incorporated by reference in its entirety.

In embodiments of the present disclosure, the needless assembly may comprise male threads that are sized and have a thread pattern that will engage with a standard ISO 594-2 type of female fitting. An example of an ISO 594-2 type of fitting is a Q-style fitting.

According to still further exemplary implementations of the embodiments of the present disclosure, a collar or a needless connector generally may bend or elastically deform in order to allow better interference fit compliance with corresponding connectors, i.e., the needless assembly.

In one or more embodiments, a female connector may be selected from the group consisting essentially of needle-free connectors, catheter luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc.

In one or more embodiments, the male connector may be an intravenous tubing end or a stopcock.

As would be readily appreciated by skilled artisans in the relevant art, while descriptive terms such as "lock", "hole", "tip", "hub", "thread", "prong", "protrusion", "insert", "tab", "wall", "top", "side", "bottom" and others are used throughout this specification to facilitate understanding, it is not intended to limit any components that can be used in combinations or individually to implement various aspects of the embodiments of the present disclosure.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

Figure 1A:
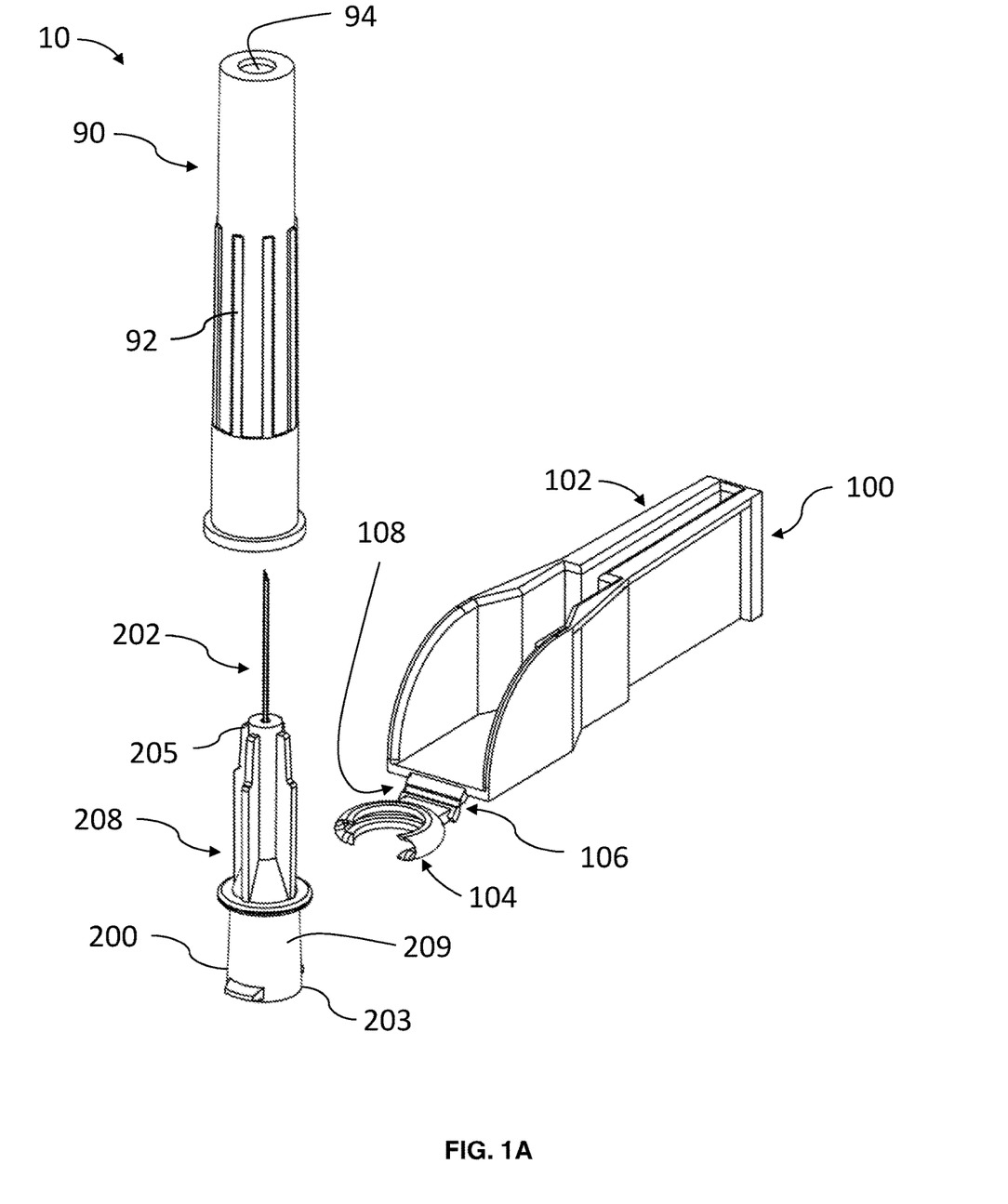
FIG. 1A is an exploded side elevation view of a needle shield system according to an embodiment of the present disclosure.
Figure 1B:
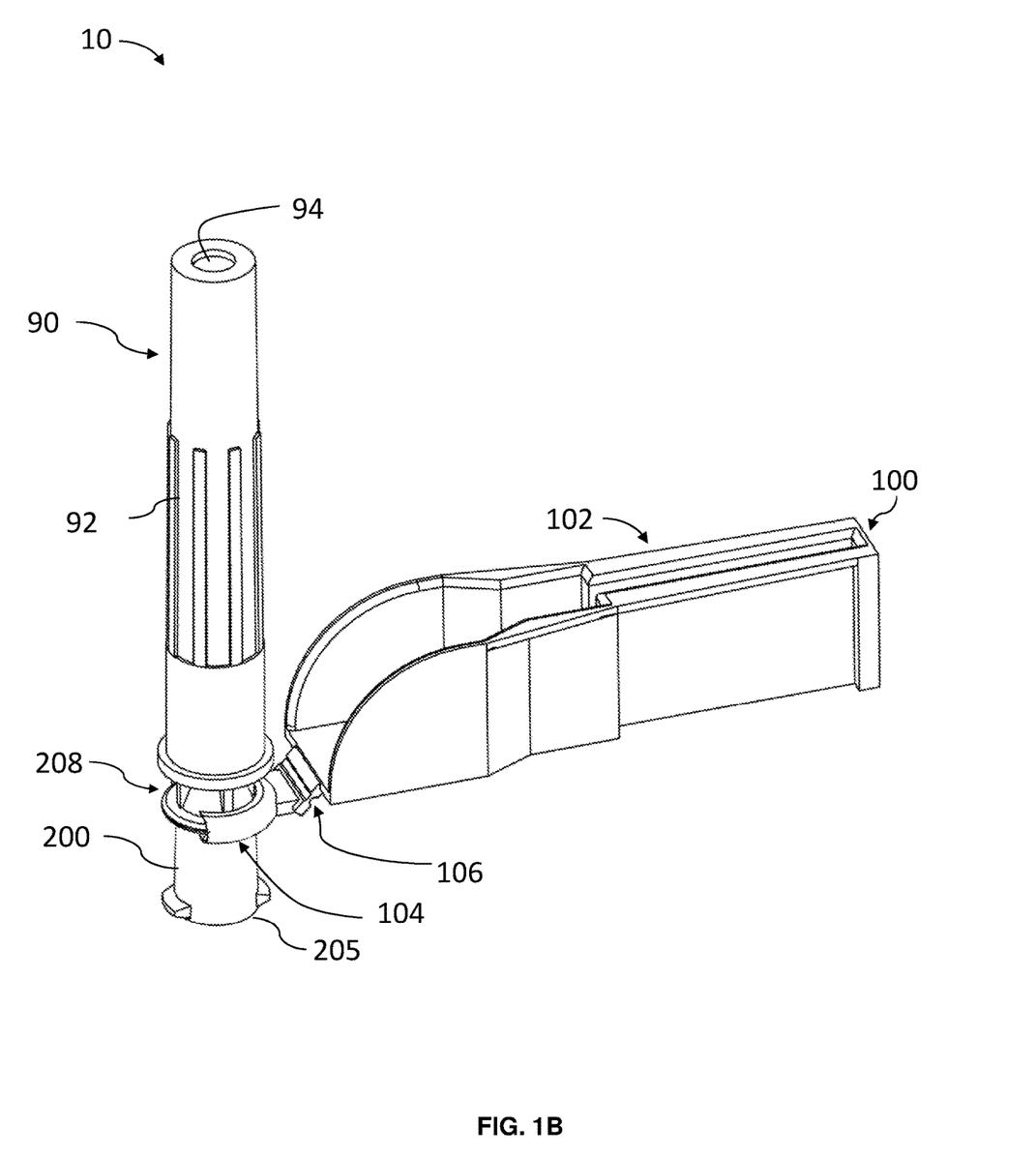
FIG. 1B is a side perspective view of the needle shield system in accordance with the embodiment as shown in FIG. 1A.

Referring to FIGS. 1A and 1B, a needle shield system 10 comprising a needle shield assembly 100 for use with a needle assembly 200 including a hub 208 and a needle cannula 202 disposed within a lumen of the hub 208, the lumen extending therethrough. The hub 208 includes an open proximal end 203, a distal end 205 and an outer surface 209, the open proximal end 203 including a cavity (not shown) therein. The lumen of the hub 208 is in fluid communication with the cavity 212. A receiving flange 210 in the form of a radial protrusion is disposed at a distance from the open proximal end 203 on the outer surface 209 of the hub 208. In one or more embodiments, the hub 208 is a conventional needle hub.

The needle shield assembly 100 comprises a shield portion 102, a hub connection portion 104 and a bridge portion 106 including a living hinge 108, the bridge portion 106 joining the hub connection portion 104 and the shield portion 102. The hub connection portion 104 comprises a partially circular receiving ring 112 forming a U-shaped cross section 126 within the partially circular receiving ring 112 of the hub connection portion 104. The U-shaped cross section provides a structure having a first diameter 126D and second diameter 124D. In one or more embodiments, the first diameter 126D is less than the second diameter 124D. As can best be seen in FIGS. 6C and 6D, a recess 124 is sized to frictionally receive and engage the receiving flange 210 of the hub 208 when the needle shield assembly 100 is advanced against the receiving flange 210 in an axial direction towards the needle assembly 200. The receiving flange 210 has a diameter 210D that is equal to or slightly less than the second diameter 124D of the recess 124 but greater than the first diameter 126D. In one or more embodiments, the partially circular receiving ring 112 defines a crescent shape having pointed ends 112P. According to one or more embodiments, "partially circular" refers to a component that defines the shape of a partial circle, but not a full circle. A partial circle comprises an arc having a length that is less than the circumference of a full circle that has the same radius of the arc. In one or more embodiments, the partially circular receiving ring 112 includes a radial or rotational locking feature, the locking feature preventing significant rotational degree of freedom between the needle shield assembly 100 and the needle assembly 200.

In one or more embodiments, the partially circular receiving ring 112 of the needle shield assembly 100 is dimensioned such that a radial interference fit with the receiving flange 210 of the needle assembly 200 locks with the partially circular receiving ring 112, such that the partially circular receiving ring 112 locks onto the receiving flange 210.

In one or more embodiments, the partially circular receiving ring 112 has a crescent shape configured to attach to the hub 208, dimensionally sized to ISO standards for a needle hub.

In one or more embodiments, a needle cap 90 is disposed over the needle cannula 202 and the hub 208. The needle cap 90 may be provided over the hub 208 during shipping and packaging and may be removed prior to use to prevent needle stick. After use, the needle cap 90 may be disposed through proper medical waste procedures, while the needle shield assembly 100 is activated and folded over the needle cannula 202, after which the needle shield assembly 100 and the needle assembly 200 may be disposed, the needle shield assembly 100 preventing needle stick. In one or more embodiments, the needle cap 90 includes a plurality of axially disposed ribs 92 on an outer surface of the needle cap 90, the plurality of axially disposed ribs 92 extending at least partially the length of the needle cap 90. The plurality of axially disposed ribs 92 aid in gripping and manipulation of the needle cap 90. In one or more embodiments, the needle cap 90 includes an air vent 94 disposed on a distal end of the needle cap 90.

Figure 2A:
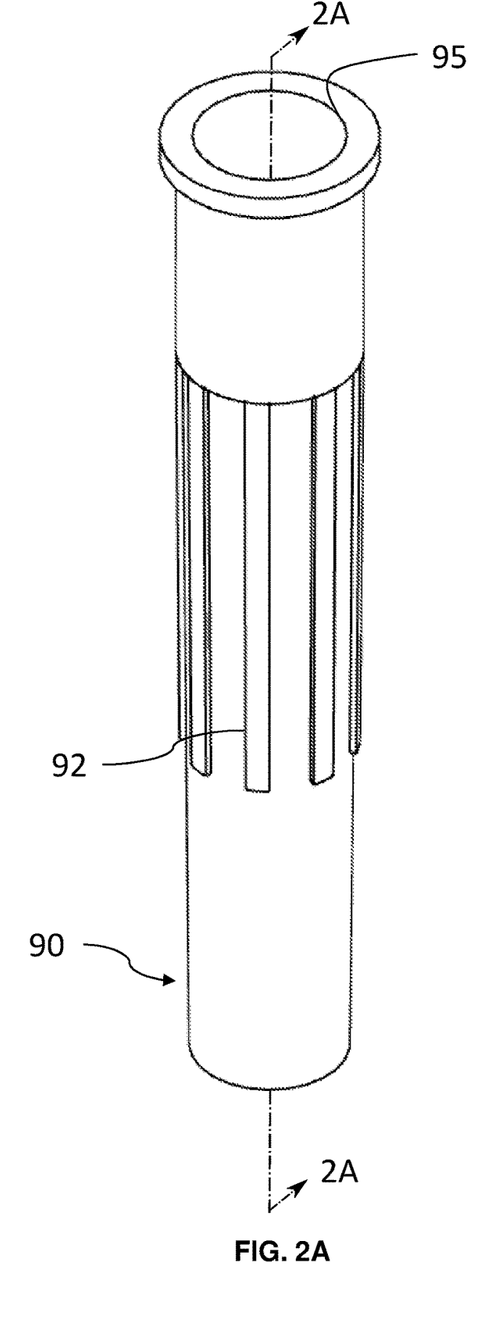
FIG. 2A is a top perspective view of a needle cap in accordance with the embodiment as shown in FIG. 1A.
Figure 2B:
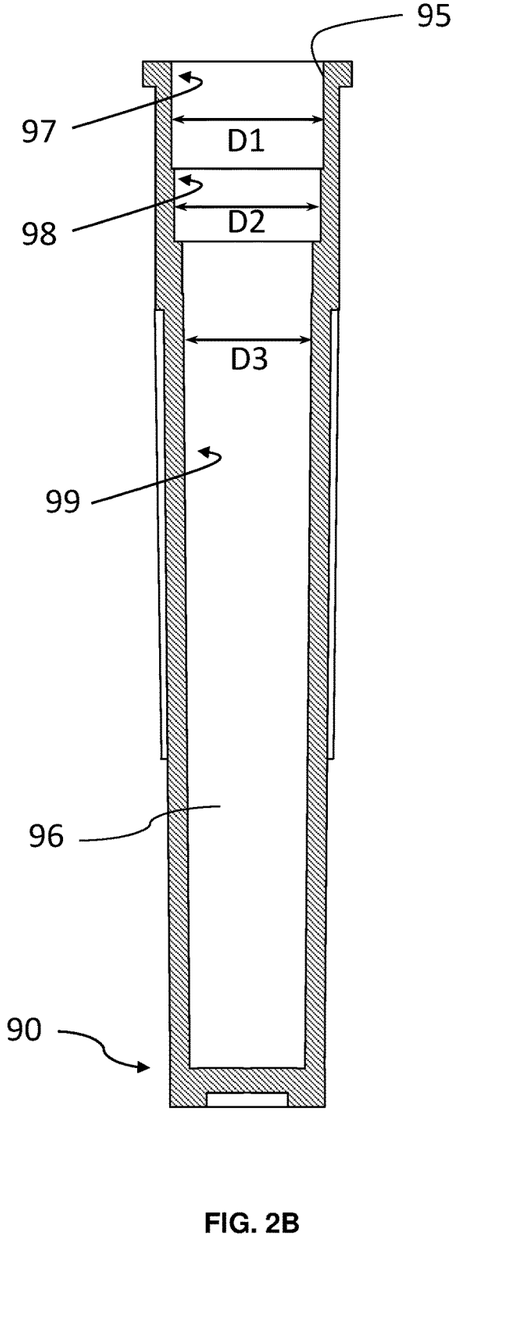
FIG. 2B is a cross-sectional view of the needle cap in accordance with the embodiment as shown in FIG. 1A taken along line 2A-2A of FIG. 2A.

As shown in FIGS. 2A and 2B, an open proximal end 95 of the needle cap 90 defines a cavity having an inner sidewall 96. The inner sidewall 96 comprises three portions adjacent to one another, a first inner sidewall portion 97 being adjacent and distal to the open proximal end 95, a second inner sidewall portion 98 being adjacent and distal to the first inner sidewall portion 97 and a third inner sidewall portion 99 being adjacent and distal to the second inner sidewall portion 98. The first inner sidewall portion 97 has a substantially cylindrical shape of a substantially constant diameter D1, the second inner sidewall portion 98 has a substantially cylindrical shape of a substantially constant diameter D2, and the third inner sidewall portion 99 has a frustoconical shape of a variable diameter D3. Diameter D1 is greater than diameters D2 and D3, and diameter D2 is greater than diameter D3. Diameter D3 is smallest at a distal end of the inner sidewall 96.

Figure 3A:
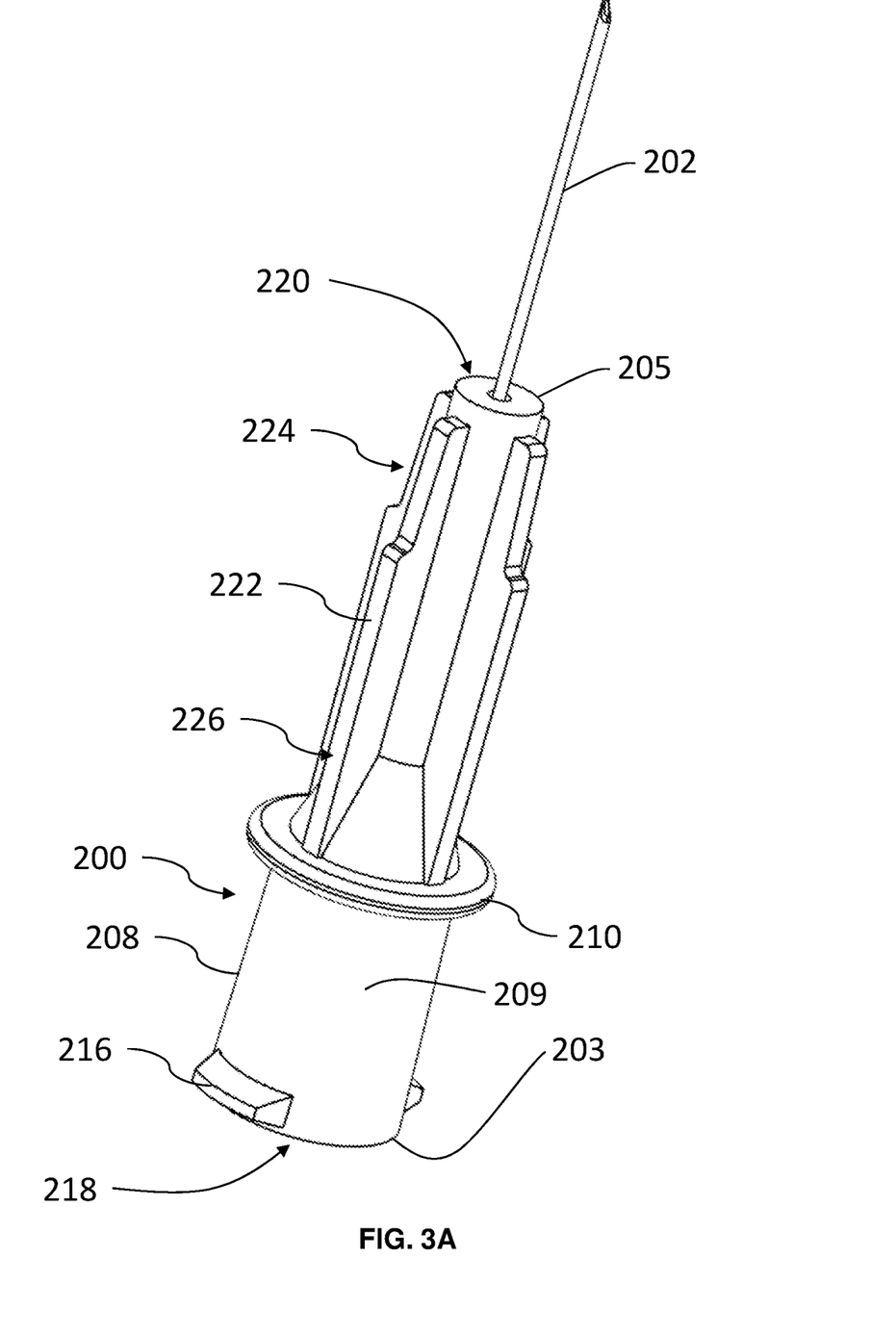
FIG. 3A is a side perspective view of a needle assembly in accordance with the embodiment as shown in FIG. 1A.
Figure 3B:
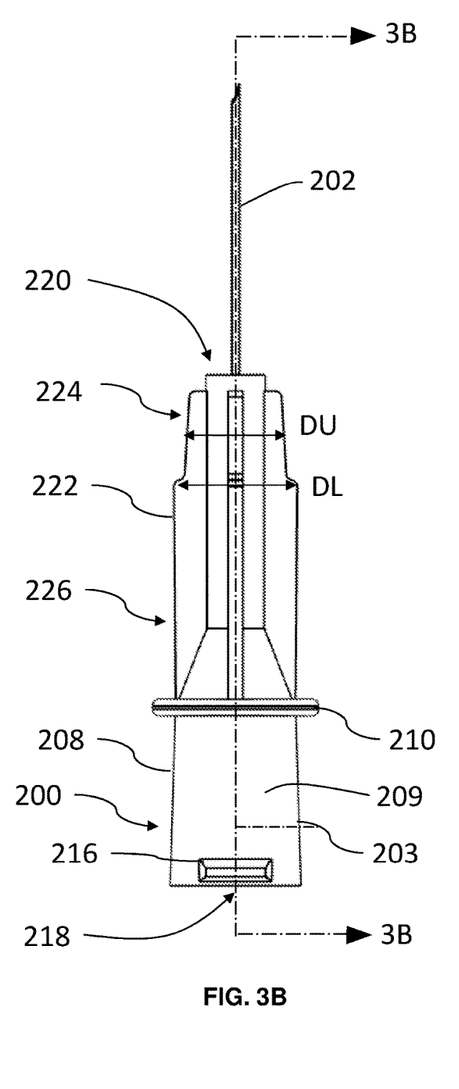
FIG. 3B is a side elevation view of the needle assembly in accordance with the embodiment as shown in FIG. 1A.
Figure 3C:
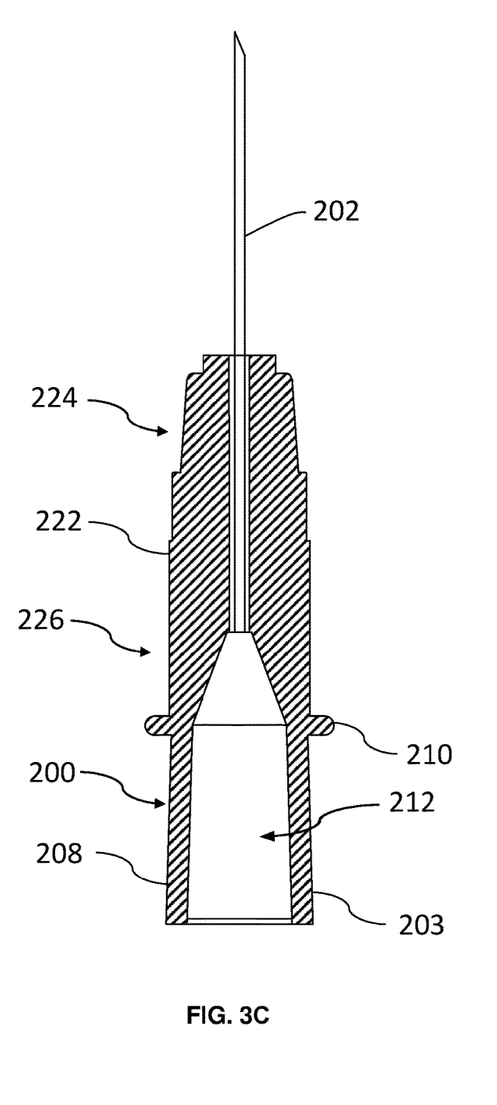
FIG. 3C is a cross-sectional view of the needle assembly in accordance with the embodiment as shown in FIG. 1A taken along line 3B-3B of FIG. 3B.

As shown in FIGS. 3A-3C, the needle assembly 200 comprises a hub 208 having the proximal end 203 and distal end 205. The lumen of the hub 208 extends through the needle assembly 200 and is in fluid communication with a cavity 212. The needle cannula 202 is non-removably disposed within the lumen of the hub 208. The cavity 212 is defined by an open proximal end, a proximal frustoconical portion and a distal conical portion, wherein the proximal frustoconical portion is configured to mate with a female luer connector, the proximal frustoconical portion including a 6% taper between the distal end and the proximal end per ISO 80369-7:2016 standards. A male luer connector thread 216 is disposed on a proximal portion 218 of an outside surface of the hub 208, the male luer connector thread 216 comprising two partial flanges. In one or more embodiments, the two partial flanges are helical in shape. The male luer connector thread 216 is configured to connect to a female luer connector of a syringe as per ISO 80369-7:2016 standards.

The outside surface of the hub 208 comprises the proximal portion 218, the receiving flange 210 and a distal portion 220. The receiving flange 210 is proximally adjacent to the proximal portion 218, and the distal portion 220 is distally adjacent to the receiving flange 210. The proximal portion 218 has a frustoconical shape. The receiving flange 210 in the depicted embodiment is configured as a radial protrusion. In one or more embodiments, the receiving flange 210 includes two flanges separated by a gap.

The distal portion 220 has at least two radially disposed ribs 222, the at least two radially disposed ribs 222 having an upper portion 224 and a lower portion 226. The upper portion 224 having a diameter DU and the lower portion 226 having a diameter DL. The diameter DU is smaller than the diameter DL. The transition from the upper portion 224 to lower portion 226 may be rounded or chamfered.

Figure 4A:
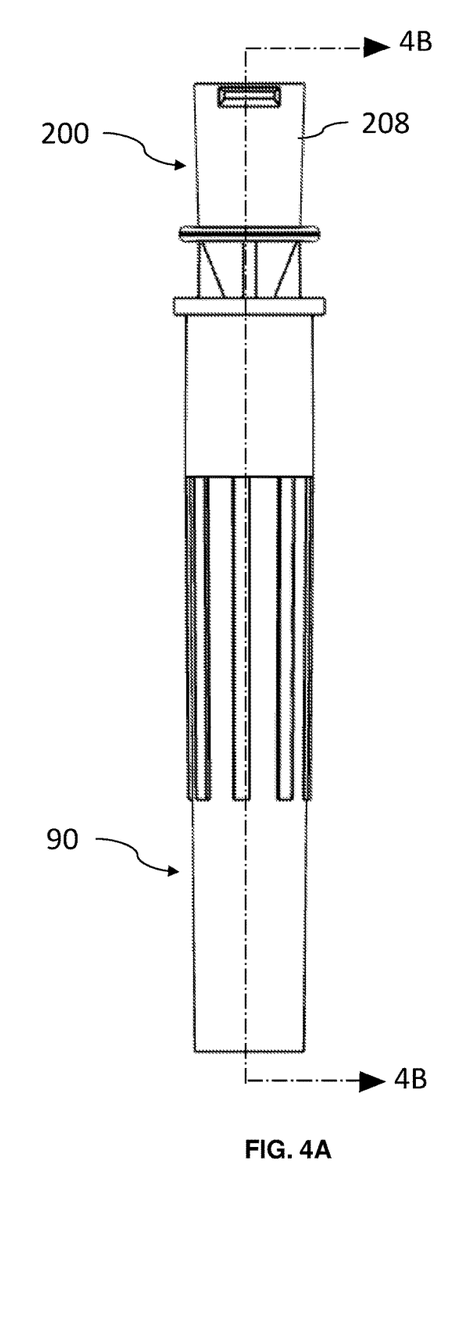
FIG. 4A is a side elevation view of the needle assembly disposed within the needle cap in accordance with the embodiment as shown in FIG. 1A.
Figure 4B:
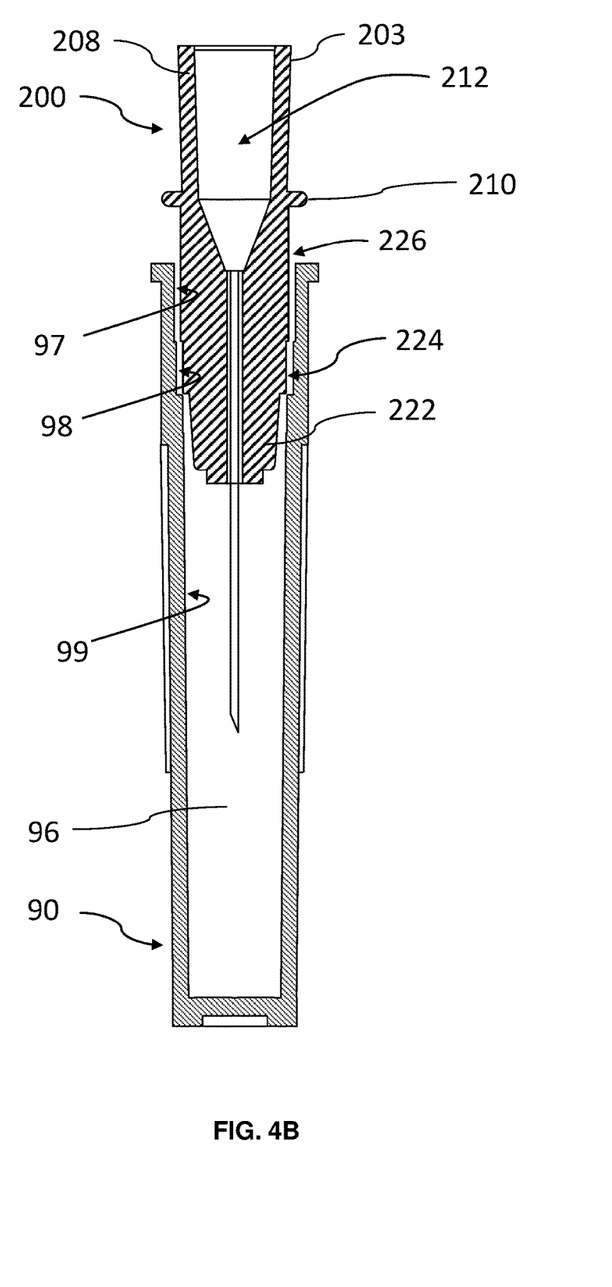
FIG. 4B is a cross-sectional view of the needle assembly disposed within the needle cap in accordance with the embodiment as shown in FIG. 1A taken along line 4B-4B of FIG. 4A.

As shown in FIGS. 4A and 4B, the needle assembly 200 is disposed within the needle cap 90. The lower portion 226 of the at least two radially disposed ribs 222 of the needle assembly 200 sits within the first inner sidewall portion 97 of the needle cap 90. The upper portion 224 of the at least two radially disposed ribs 222 of the needle assembly 200 sits within the second inner sidewall portion 98.

The diameter D1 of the first inner sidewall portion 97 of the needle cap 90 and the diameter DL of the lower portion 226 of the at least two radially disposed ribs 222 of the needle assembly 200 are substantially equal, or the diameter DL is slightly larger than the diameter D1 as to create an interference fit. Likewise, the diameter D2 of the second inner sidewall portion 98 of the needle cap 90 and the diameter DU of the upper portion 224 of the at least two radially disposed ribs 222 of the needle assembly 200 are substantially equal, or the diameter DU is slightly larger than the diameter D2 as to create an interference fit.

Figure 5A:
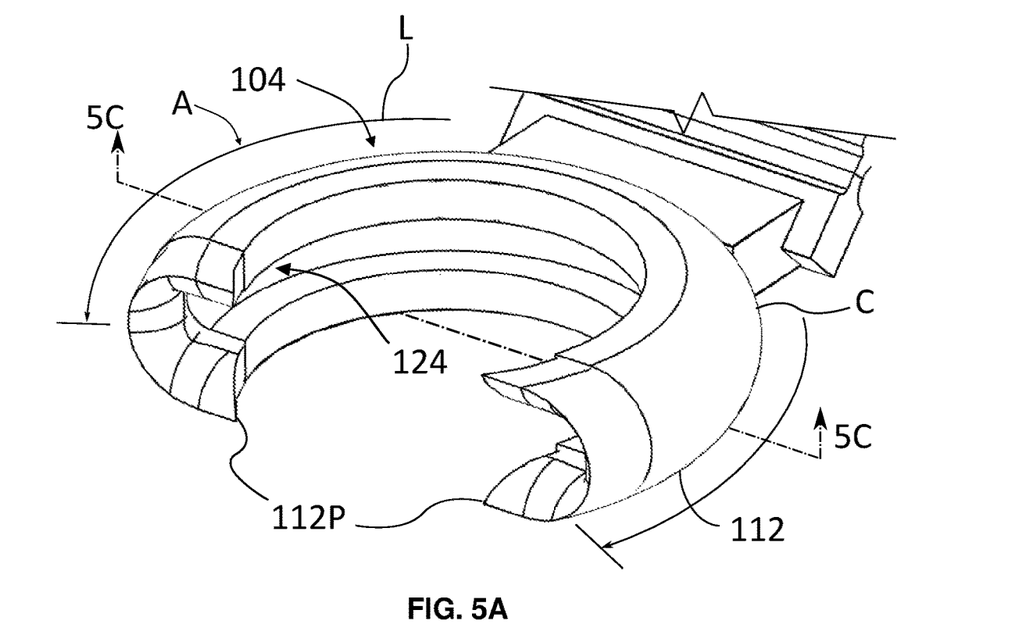
FIG. 5A is a top perspective view of a hub connection portion of a needle shield assembly in accordance with the embodiment as shown in FIG. 1A.
Figure 5B:
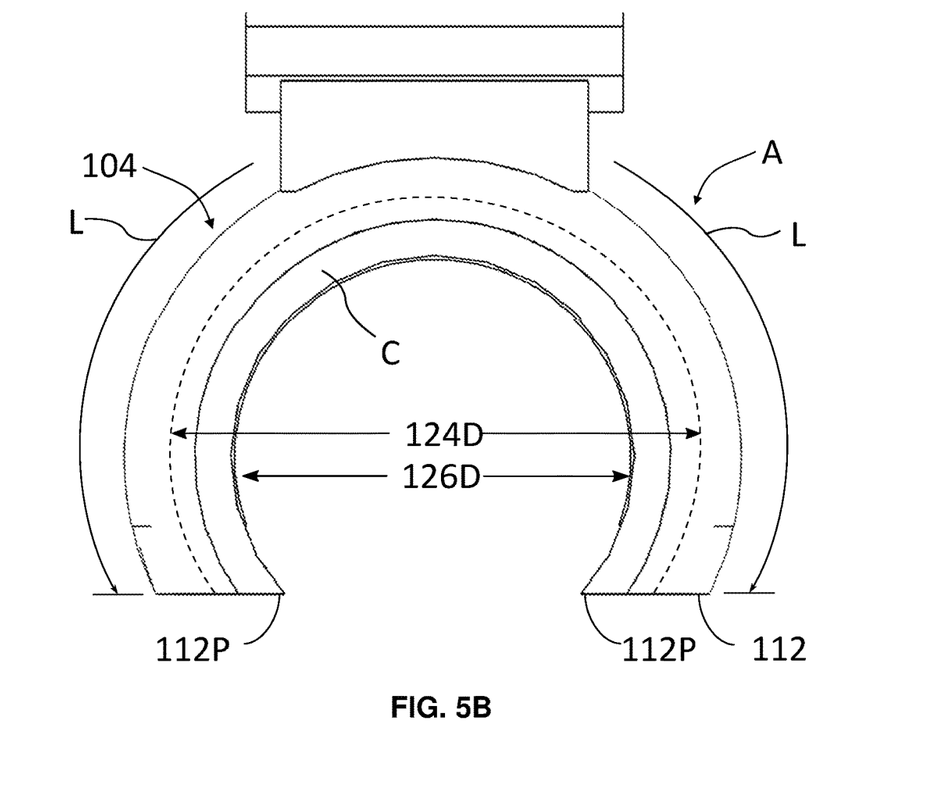
FIG. 5B is a top view of the hub connection portion of the needle shield assembly in accordance with the embodiment as shown in FIG. 1A.
Figure 5C:
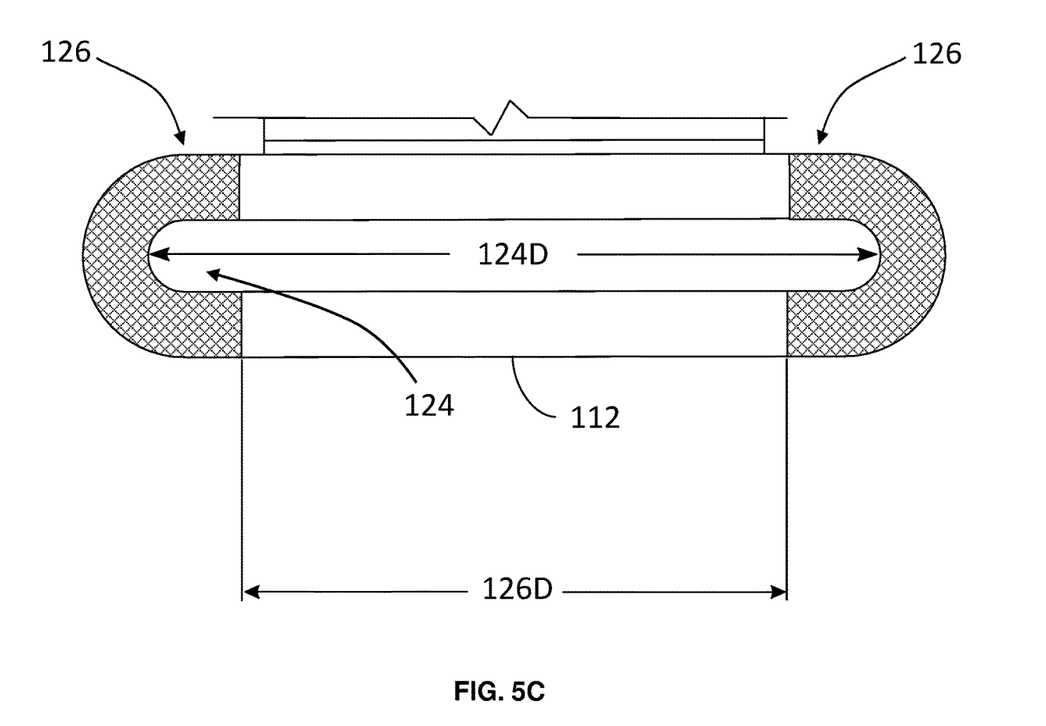
FIG. 5C is a cross-sectional view of the hub connection portion of the needle shield assembly in accordance with the embodiment as shown in FIG. 1A taken along line 5C-5C of FIG. 5A.

As shown in FIG. 5A-5C, in one or more embodiments, the hub connection portion 104 comprises a partially circular receiving ring 112 that is circularly-shaped and defines a partial circle. In one or more embodiments, the partially circular receiving ring 112 defines an arc A of a circle C having an arc length L that is less than the circumference of the circle C defined by the receiving ring 112. In one or more embodiments, the arc A is greater than 50% and less than 90%, less than 80% or less than 70% of the circle C defined by the receiving ring 112. In some embodiments, the receiving ring 112 defines a crescent shape having pointed ends 112P and an arc A having a length L that is greater than the circumference of a semicircle having a same radius as the arc A and less than the circumference of a full circle having the same radius as the arc A. In some embodiments, the partially circular receiving ring 112 deflects or elastically deforms outwardly upon advancement of the receiving flange 210 of the needle assembly 200. The crescent shape performs similar to a pair of hooks which removably lock the receiving flange 210 of the needle assembly 200 within. In one or more embodiments, the partially circular receiving ring 112 further includes a recess 124, the recess 124 forming a U-shaped cross section 126 within the partially circular receiving ring 112 of the hub connection portion 104. The recess 124 defines the first diameter 126D, which is less than the second diameter 124D so that the receiving flange 210 of the needle assembly 200 snugly fits in the recess 124 and is held in place by the recess 124.

As shown in FIG. 6A-6D, the receiving flange 210 of the needle assembly 200 is received within the partially circular receiving ring 112 of the needle shield assembly 100. The partially circular receiving ring 112 deflects or elastically deforms from an initial state upon advancement of the receiving flange 210 and snap-fits the receiving flange 210 upon full advancement, wherein the partially circular receiving ring 112 deflects or elastically deforms back into the initial state. The snap-fit fitment allows for retention of the receiving flange 210 within the partially circular receiving ring 112, but still allows for twisting and angular movement of the partially circular receiving ring 112 around the receiving flange 210. Thus, a practitioner may position the partially circular receiving ring 112 and the needle shield assembly 100 at any angle relative to an insertion site of a patient's skin. The practitioner may also position the partially circular receiving ring 112 and the needle shield assembly 100 at any angle relative to the practitioner's line of sight; thereby permitting unobstructed viewing of fluid withdraw from a vial container or unobstructed viewing of the insertion site of a patient's skin.

This configuration permits a proper or a preferred orientation of a needle bevel on the needle cannula 202 to be varied depending on a particular medical procedure. For example, subcutaneous, intravenous or intradermal types of injections typically require the needle to be inserted at various angles in relation to the patient's skin (e.g., 45 degrees, 25 degrees, 10 degrees respectively), with the needle bevel typically in the up position (facing away from the skin surface) and the needle bevel visible to the clinician. As such, it is advantageous for the needle assembly 200 relative to the needle shield assembly 100 to be rotated to a position such that the needle bevel is not obstructing the practitioner's view of the needle bevel. In intermuscular injection, the bevel is typically 90 degrees to the patient's skin.

Figures 6A, 6B:
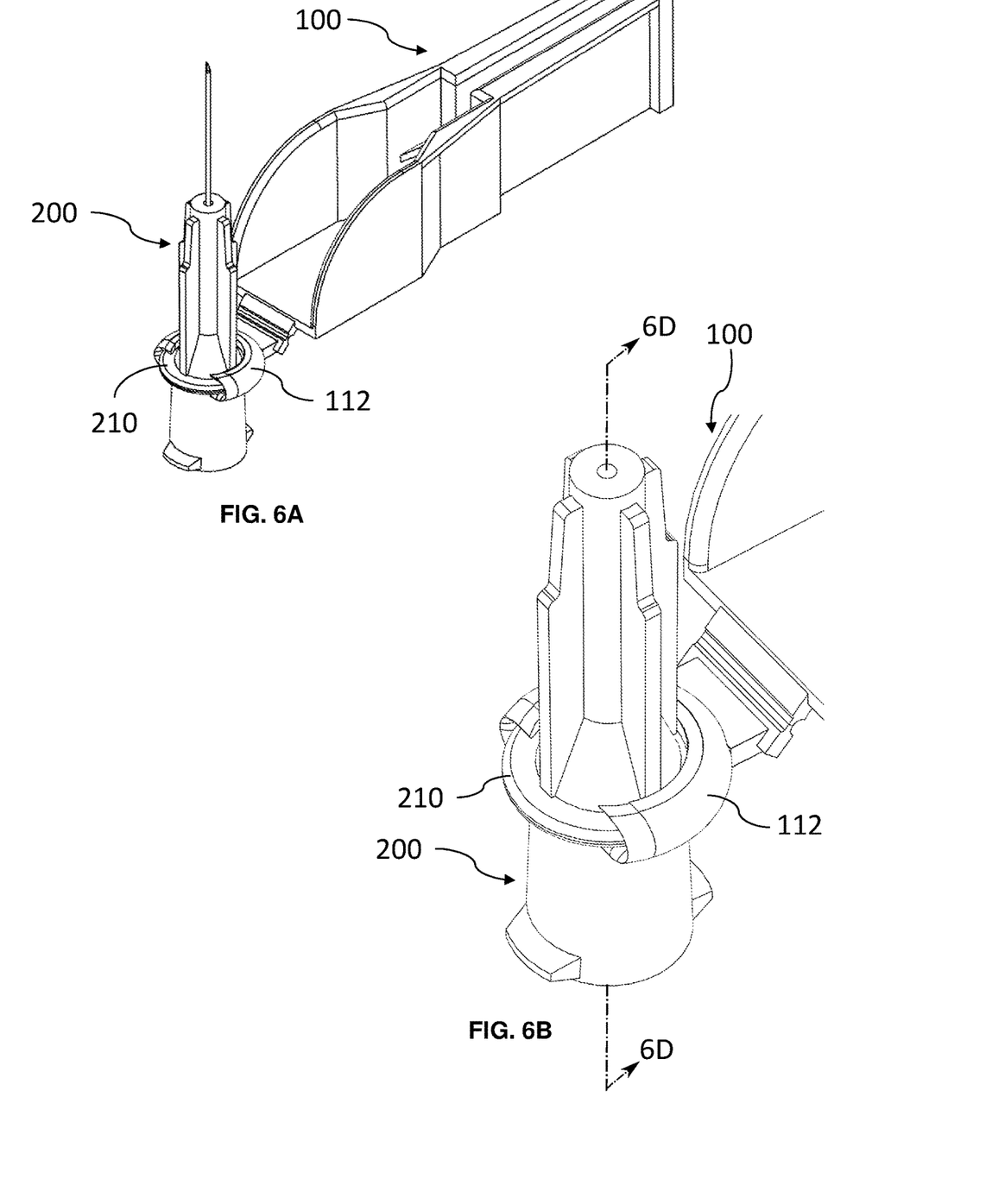
FIG. 6A is a top perspective view of the needle shield assembly in accordance with the embodiment as shown in FIG. 1A.
FIG. 6B is a detailed top perspective of the needle shield assembly in accordance with the embodiment as shown in FIG. 1A.
Figure 6C:
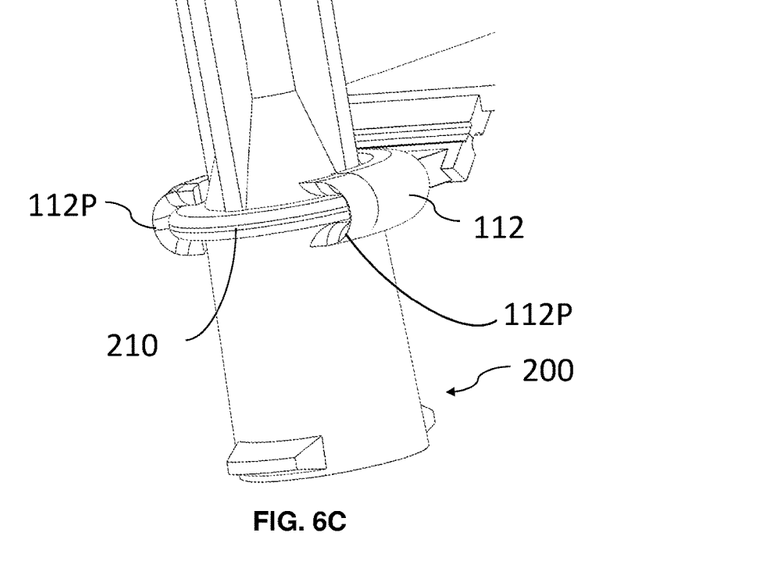
FIG. 6C is a detailed side perspective view of the needle shield assembly in accordance with the embodiment as shown in FIG. 1A.
Figure 6D:
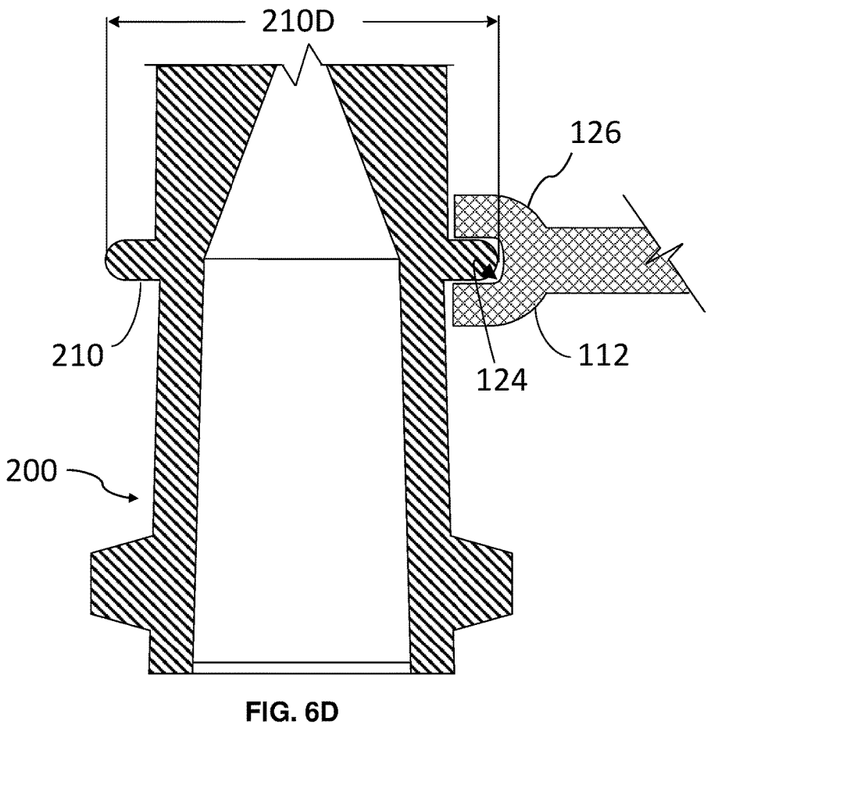
FIG. 6D is a cross-sectional view of the needle shield assembly in accordance with the embodiment as shown in FIG. 1A taken along line 6D-6D of FIG. 6B.

As shown in FIG. 6D, the partially circular receiving ring 112 envelops more than half of a profile of the receiving flange 210, the receiving flange 210 being in the form of a circular protrusion extending from the outer surface 209 of the needle assembly 200. The circular protrusion sits within the recess 124 of the partially circular receiving ring 112, the U-shaped cross-section 126 of the recess 124 having a slightly larger height and width than the receiving flange 210.

Figure 7A:
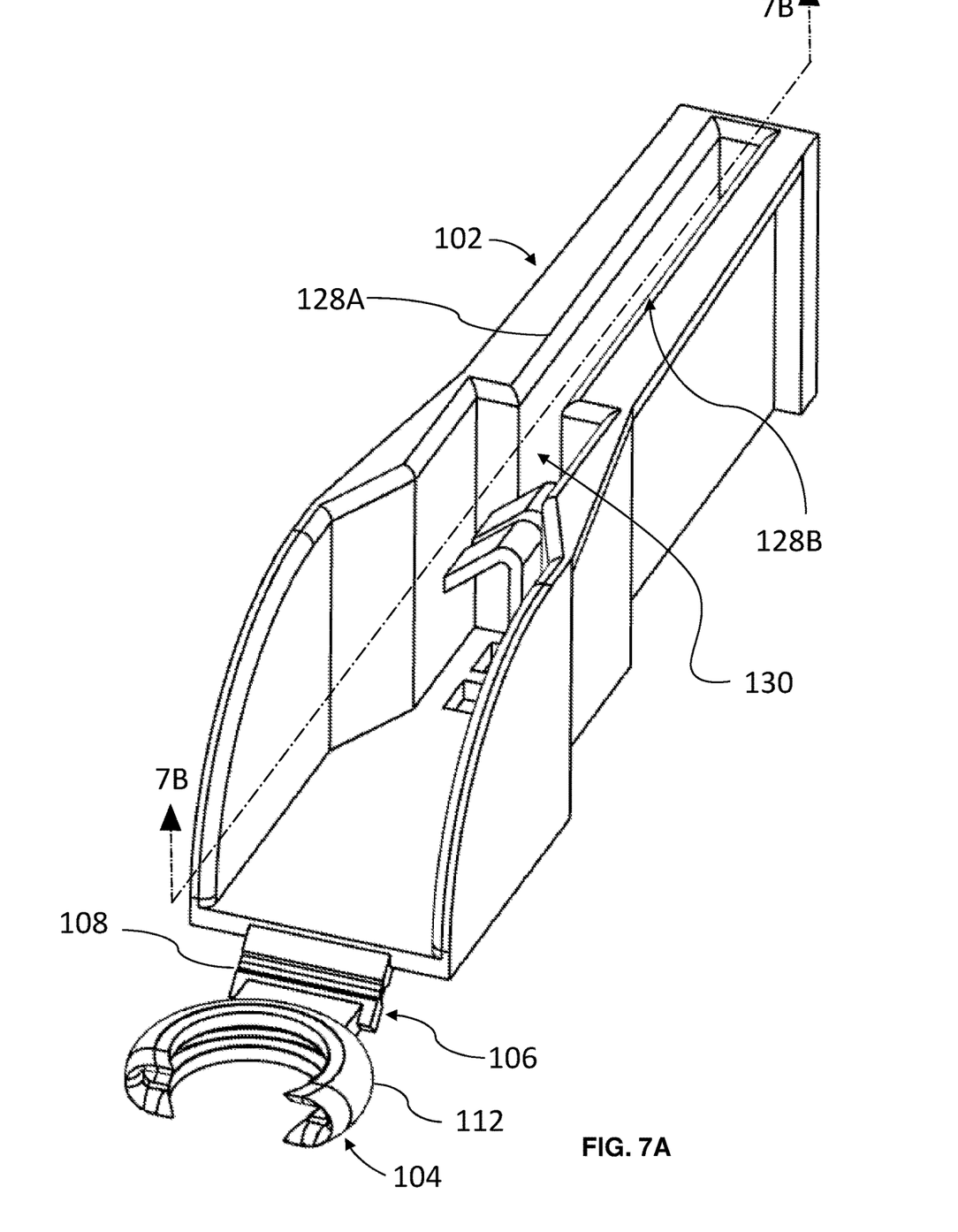
FIG. 7A is top perspective view of the needle shield assembly in accordance with the embodiment as shown in FIG. 1A.
Figure 7B:
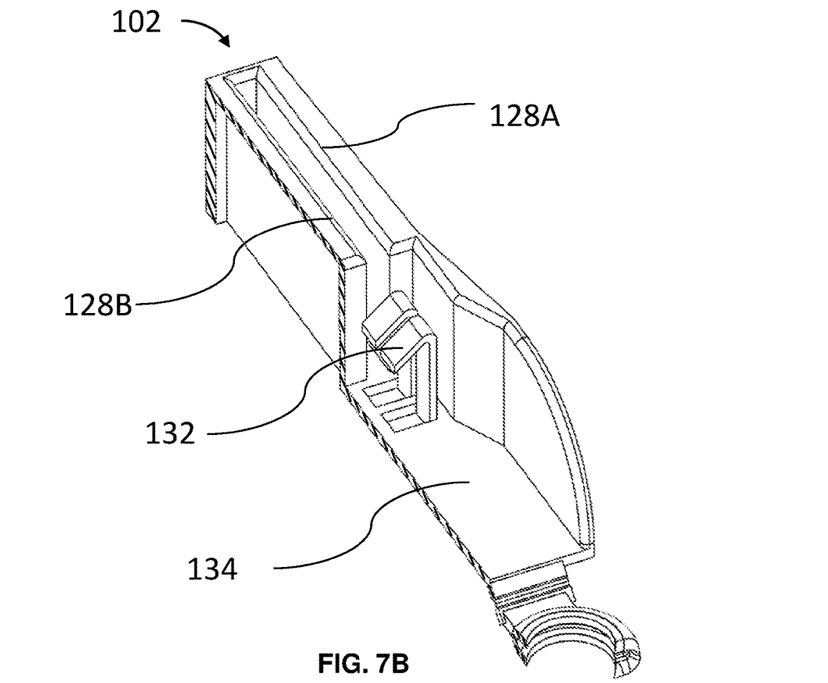
FIG. 7B is a cross-sectional view of the needle shield assembly in accordance with the embodiment as shown in FIG. 1A taken along line 7B-7B of FIG. 7A.

As shown in FIGS. 7A and 7B, the shield portion 102 comprises two longitudinal walls 128A and 128B extending from a base 134, the two longitudinal walls 128A and 128B being separated by a needle assembly receiving cavity 130, the needle assembly receiving cavity 130 being defined by the base 134, the two longitudinal walls 128A and 128B and an open end opposite the base 134. The two longitudinal walls 128A and 128B, and the needle assembly receiving cavity 130 are configured to receive the needle assembly 200, wherein a proximal portion of the needle assembly receiving cavity 130 is wider than a distal portion of the needle assembly receiving cavity 130. The proximal portion of the needle assembly receiving cavity 130 is wide enough to receive the hub 208 of the needle assembly 200. The distal portion of the needle assembly receiving cavity 130 is wide enough to receive the needle cannula 202. Disposed within the proximal portion of the needle assembly receiving cavity 130 is at least one locking hook 132. The at least one locking hook 132 is in the same plane as a second of the at least one locking hook 132. The at least one locking hook 132 is a protrusion extending from the base 134. The at least one locking hook 132 is configured to deflect or elastically deform upon engagement with the needle cannula 202. The at least one locking hook 132 has a pointed end which first engages the needle cannula 202.

Figure 8:
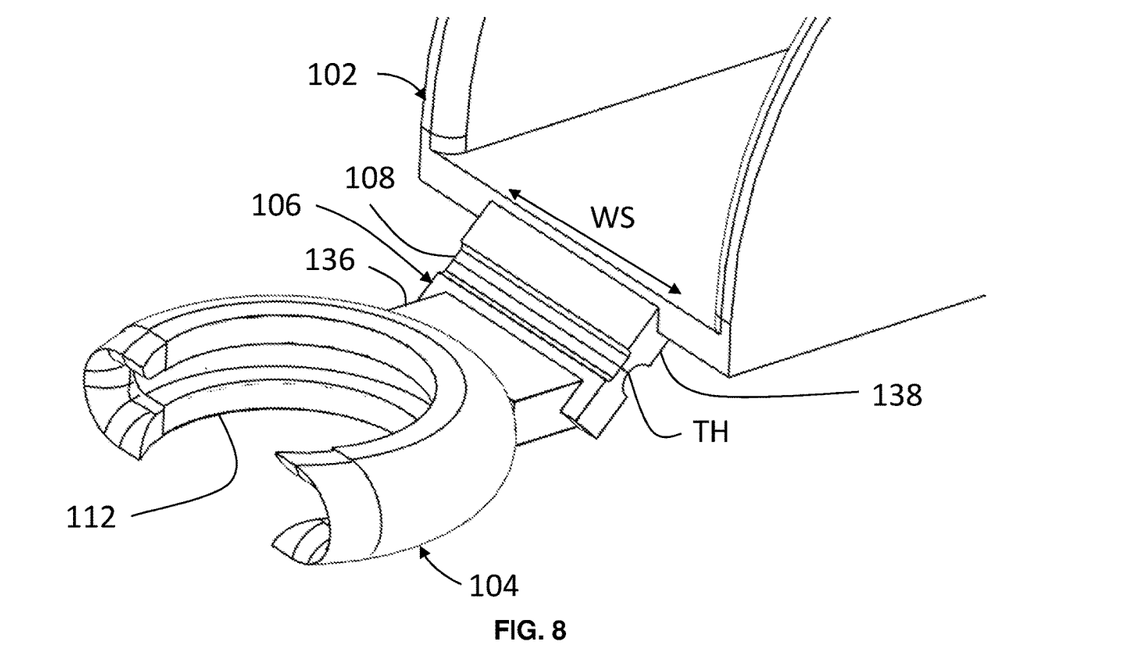
FIG. 8 is a detailed side perspective view of the needle shield assembly in accordance with the embodiment as shown in FIG. 1A.

As shown in in FIG. 8, the bridge portion 106 comprises a first portion 136 joining the bridge portion 106 to the shield portion 102 of the needle shield assembly 100 and a second portion 138 joining the bridge portion 106 to the partially circular receiving ring 112. The first portion 136 and the second portion 138 are separated by the living hinge 108. In one or more embodiments, the first portion 136 and the second portion 138 each comprise a width WS, and the living hinge 108 comprises a thickness TH. If the thickness of the living hinge 108 TH is too great, the living hinge 108 will not be flexible enough, and the shield portion 102 will not be easily closed over the needle assembly 200. On the other hand, if the thickness of the living hinge 108 TH is too small, the living hinge 108 will be prone to breaking or snapping.

Figure 9:
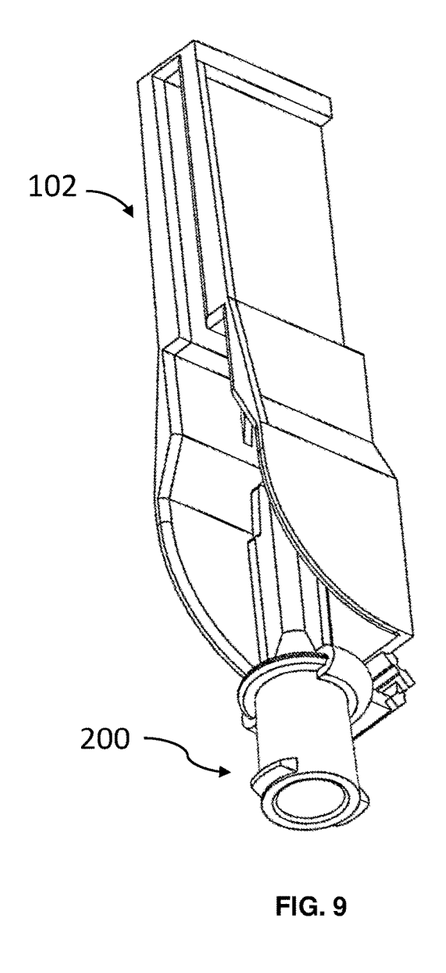
FIG. 9 is a side perspective view of the needle shield assembly in a closed position in accordance with the embodiment as shown in FIG. 1A.
Figure 10:
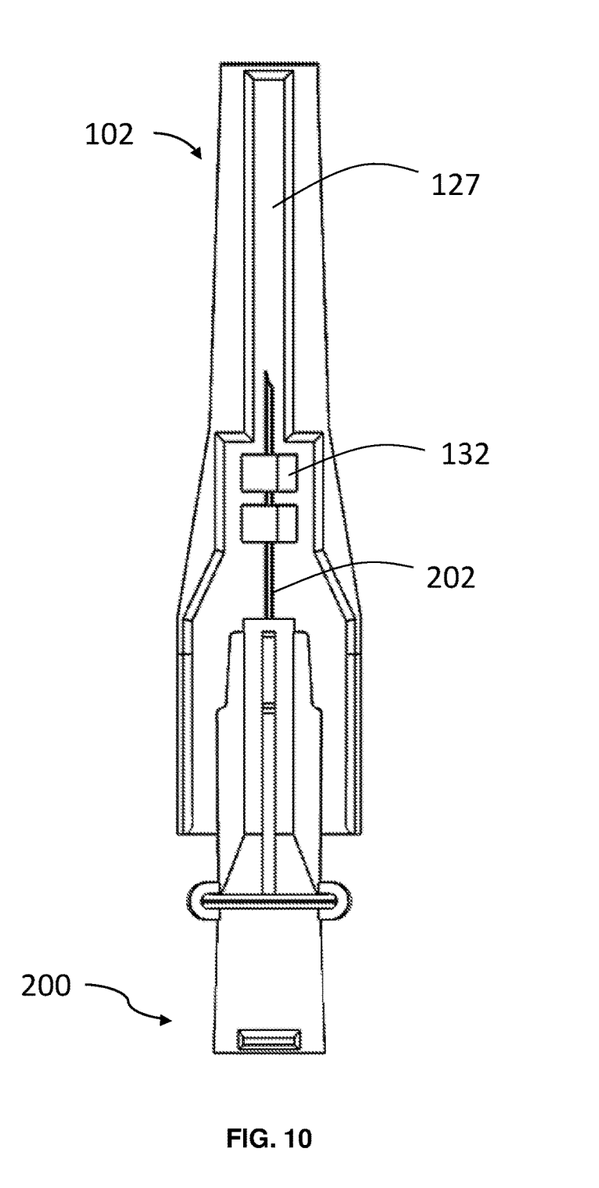
FIG. 10 is a top view of the needle shield assembly in a closed position in accordance with the embodiment as shown in FIG. 1A.

A medical practitioner can grip the shield portion 102 and pivot the shield portion 102 toward the needle assembly 200 from an open position as shown in FIG. 6A to a closed position as shown in FIGS. 9 and 10. As shown in FIG. 10, the at least one locking hook 132 locks the needle cannula 202, thereby preventing opening of the shield portion 102.

In one or more embodiments, the shield portion 102, the bridge portion 106, the hub connection portion 104 and the living hinge 108 comprise a unitary structure integrally molded of thermoplastic material.

In an exemplary use of the disclosure, a practitioner unpacks a needle shield assembly 100 from packaging in an open position. The practitioner assembles and secures a syringe to hub 208 of needle assembly 200. Once syringe 310 has been engaged with the hub 208, the needle cap 90 is removed from the needle assembly 200 and injection occurs. The practitioner removes the needle cannula 202 from the patient. Either with or without the syringe 310 secured to the hub 208 of the needle assembly 200, practitioner rotates the hub connection portion 104 about the bridge portion 106 to toggle the needle shield assembly 100 from the open position to the closed position. In the closed position, the at least one locking hook 132 is fully engaged, thus shielding the needle cannula 202 from accidental post-injection needle sticks.

In one or more embodiments, toggling the needle shield assembly 100 from the open position to the closed position may be completed in a variety of ways. During injection, the practitioner may be required to use one hand to press the injection site with a sanity cloth or pad during or after injection. The practitioner can remove the needle cannula 202 from the skin and single-handedly toggle the needle shield assembly 100 by rotating the needle shield assembly 100 around the hub 208 of the needle assembly 200.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A needle shield assembly for use with a needle assembly comprising:
a shield portion comprising two longitudinal walls extending from a base of the shield portion, the two longitudinal walls being separated by a needle assembly receiving cavity, the needle assembly receiving cavity being defined by the base, the two longitudinal walls and an open end opposite the base, the two longitudinal walls and needle assembly receiving cavity being configured to receive a needle assembly, wherein a proximal portion of the needle assembly receiving cavity is wider than a distal portion of the needle assembly receiving cavity, the proximal portion of the needle assembly receiving cavity receiving a hub of the needle assembly and the distal portion of the needle assembly receiving cavity receives a needle cannula of the needle assembly;
a removable needle cap disposed over the needle cannula of the needle assembly and the hub of the needle assembly, the removable needle cap having an open proximal end defining a cavity, the cavity having an inner sidewall, the inner sidewall comprising a first inner sidewall portion being adjacent and distal to the open proximal end of the cavity, a second inner sidewall portion being adjacent and distal to the first inner sidewall portion and a third inner sidewall portion being adjacent and distal to the second inner sidewall portion, the first inner sidewall portion having a constant first diameter, the second inner sidewall portion having a substantially cylindrical shape of a constant second diameter, and the third inner sidewall portion having a frustoconical shape of a variable third diameter, the first diameter of the first inner sidewall portion is greater than both the second diameter of the second inner sidewall portion and the third diameter of the third inner sidewall portion, and second diameter of the second inner sidewall portion is greater than the third diameter of the third inner sidewall portion, the third diameter of the third inner sidewall portion is smallest at a distal end of the inner sidewall of the cavity;
a hub connection portion comprising a partially circular receiving ring defining an arc having a length that is greater than a length of an arc of a semicircle of a same radius as the arc of the partially circular receiving ring, wherein the partially circular receiving ring deflects or elastically deforms outwardly upon advancement of a receiving flange of the needle assembly, the partially circular receiving ring having a recess including a first diameter of the recess being less than a second diameter of the recess such that the recess is crescent-shape with pointed ends, wherein the receiving flange of the needle assembly is configured to receive the partially circular receiving ring of the needle shield assembly, the cross-section of the recess of the partially circular receiving ring is dimensioned to having a larger height and width than the receiving flange of the needle assembly to allow twisting and angular movement of the partially circular receiving ring around the receiving flange, the receiving flange of the needle assembly having a diameter that is equal to or slightly less than the second diameter of the recess of the partially circular receiving ring but greater than the first diameter of the recess of the partially circular receiving ring such that the partially circular receiving ring locks the receiving flange of the needle assembly within and allows twisting and angular movement of the partially circular receiving ring around the receiving flange;

two locking hooks disposed within the proximal portion of the needle assembly receiving cavity, wherein each of the two locking hooks is a protrusion extending from the base; and a bridge portion including a living hinge, the bridge portion connecting the shield portion and the hub connection portion.

2. The needle shield assembly of claim 1, wherein the hub connection portion comprises the partially circular receiving ring having a diameter sized to frictionally receive the receiving flange of the needle assembly when the needle shield assembly is advanced against the receiving flange in an axial direction towards the needle assembly.

3. The needle shield assembly of claim 2, wherein the receiving flange of the needle assembly and the hub connection portion of the needle shield assembly engage in an interference fit.

4. The needle shield assembly of claim 1, wherein each of the two locking hooks is configured to deflect or elastically deform upon engagement with the needle cannula, each of the locking hooks having a pointed end which first engages the needle cannula.

5. The needle shield assembly of claim 1, wherein the bridge portion includes a first portion and a second portion separated by the living hinge, each of the first portion and the second portion comprising a width and the living hinge comprising a thickness, the thickness being sufficient to allow the living hinge to flex and bend.

6. The needle shield assembly of claim 1, wherein the shield portion pivots against the living hinge.

7. The needle shield assembly of claim 6, wherein the shield portion pivots from an open position to a closed position.

8. The needle shield assembly of claim 7, wherein the shield portion is in the closed position when the needle cannula of the needle assembly is fully disposed within the needle assembly receiving cavity.

9. The needle shield assembly of claim 1, wherein the partially circular receiving ring further includes a recess, wherein the recess forms a U-shaped cross section within the partially circular receiving ring of the hub connection portion.

10. The needle shield assembly of claim 9, wherein the partially circular receiving ring envelopes more than half of a profile of the receiving flange of the needle assembly, the receiving flange comprising a circular protrusion extending from an outer surface of the needle assembly.

11. The needle shield assembly of claim 10, wherein the circular protrusion of the needle assembly sits within the recess of the partially circular receiving ring.

12. The needle shield assembly of claim 1, the partially circular receiving ring deflecting or elastically deforming from an initial state upon advancement of the receiving flange and snap-fitting the receiving flange upon full advancement, wherein the partially circular receiving ring deflects or elastically deforms back into the initial state.

13. The needle shield assembly of claim 1, wherein a snap-fit fitment between the receiving flange and the partially circular receiving ring allows for retention of the receiving flange within the partially circular receiving ring.

14. The needle shield assembly of claim 13, wherein the snap-fit fitment allows for twisting and angular movement of the partially circular receiving ring around the receiving flange.

15. The needle shield assembly of claim 1, wherein the partially circular receiving ring includes a radial or rotational locking feature, the locking feature preventing significant rotational degree of freedom between the needle shield assembly and the needle assembly.

16. The needle shield assembly of claim 1, wherein a distal portion of the hub comprises at least two radially disposed ribs, the at least two radially disposed ribs having an upper portion and a lower portion, wherein the upper portion having a diameter smaller than a diameter of the lower portion.

17. The needle shield assembly of claim 16, wherein the needle assembly is disposed within the needle cap, the lower portion of the at least two radially disposed ribs of the needle assembly sits within the first inner sidewall portion of the needle cap, the upper portion of the at least two radially disposed ribs of the needle assembly sits within the second inner sidewall portion.

18. The needle shield assembly of claim 16, wherein the diameter of the lower portion of the at least two radially disposed ribs of the needle assembly is slightly larger the diameter of the first inner sidewall portion of the needle cap to create an interference fit and the diameter of the upper portion of the at least two radially disposed ribs of the needle assembly is slightly larger than the diameter of the second inner sidewall portion of the needle cap to create an interference fit.

19. The needle shield assembly of claim 16, wherein each of the two locking hooks extending from the base engage the upper portion of the least two radially disposed ribs of the needle assembly.

* * * * *